(12) United States Patent
Kim et al.

(10) Patent No.: US 11,294,014 B2
(45) Date of Patent: Apr. 5, 2022

(54) METHODS AND SYSTEMS FOR REAL-TIME 3D MRI

(71) Applicants: Taeho Kim, St. Louis, MO (US); Chunjoo Park, St. Louis, MO (US)

(72) Inventors: Taeho Kim, St. Louis, MO (US); Chunjoo Park, St. Louis, MO (US)

(73) Assignee: Washington University, St. Louis, MO (US)

( * ) Notice: Subject to any disclaimer, the term of this patent is extended or adjusted under 35 U.S.C. 154(b) by 206 days.

(21) Appl. No.: 16/813,727

(22) Filed: Mar. 9, 2020

(65) Prior Publication Data

US 2020/0284866 A1 Sep. 10, 2020

Related U.S. Application Data

(60) Provisional application No. 62/880,210, filed on Jul. 30, 2019, provisional application No. 62/815,194, filed on Mar. 7, 2019.

(51) Int. Cl.
| | |
|---|---|
| *G01R 33/565* | (2006.01) |
| *G01R 33/48* | (2006.01) |
| *G01R 33/561* | (2006.01) |
| *G06N 3/08* | (2006.01) |
| *G06T 7/00* | (2017.01) |
| *A61B 5/055* | (2006.01) |
| *G06T 19/20* | (2011.01) |

(52) U.S. Cl.
CPC ........ *G01R 33/56509* (2013.01); *A61B 5/055* (2013.01); *G01R 33/4822* (2013.01); *G01R 33/5619* (2013.01); *G06N 3/08* (2013.01); *G06T 7/0016* (2013.01); *G06T 19/20* (2013.01); *G06T 2207/10088* (2013.01); *G06T 2207/20081* (2013.01); *G06T 2207/30168* (2013.01); *G06T 2210/41* (2013.01)

(58) Field of Classification Search
CPC ........... G01R 33/5509; G01R 33/4822; G01R 33/5619; G06N 3/08; G06T 7/0016; G06T 19/20; A61B 5/055
See application file for complete search history.

(56) References Cited

U.S. PATENT DOCUMENTS

| | | | |
|---|---|---|---|
| 2015/0091563 A1* | 4/2015 | Lu | A61B 5/055 |
| | | | 324/309 |
| 2017/0007148 A1* | 1/2017 | Kaditz | A61B 5/055 |
| 2019/0347772 A1* | 11/2019 | Zhang | G01R 33/561 |
| 2020/0318166 A1* | 10/2020 | Stamatoyannopoulos | |
| | | | G01N 33/5008 |
| 2021/0042883 A1* | 2/2021 | Zhang | A61B 5/055 |
| 2021/0076972 A1* | 3/2021 | Novikov | G01R 33/4808 |
| 2021/0244374 A1* | 8/2021 | Zhao | A61B 6/5282 |

* cited by examiner

*Primary Examiner* — Dixomara Vargas

(57) ABSTRACT

Among the various aspects of the present disclosure is the provision of methods and systems for real-time 3D MRI that combines dynamic keyhole data sharing with super-resolution imaging methods to improve real-time 3D MR images in the presence of motion.

19 Claims, 10 Drawing Sheets

FIG. 5A
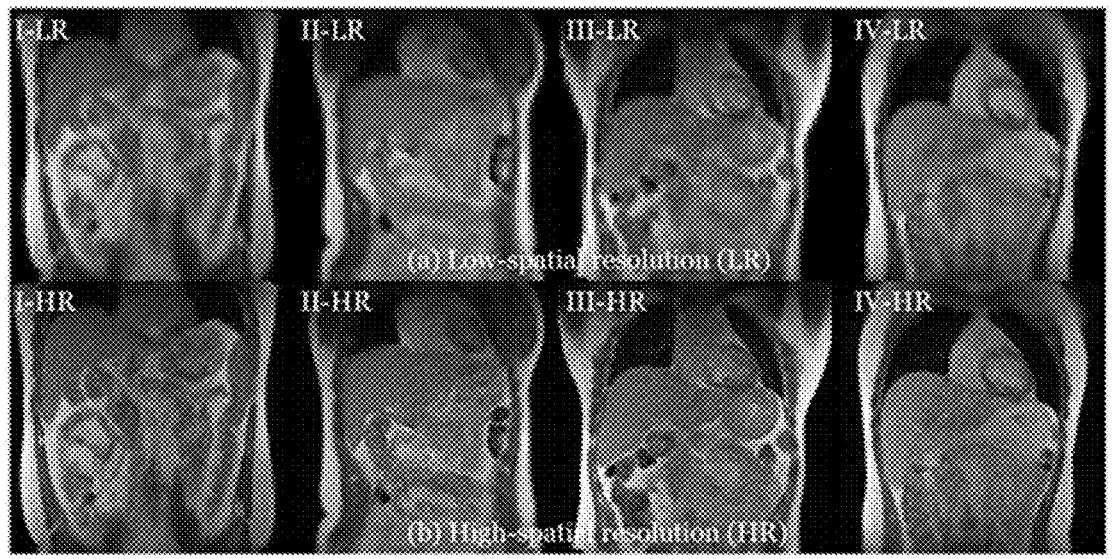
FIG. 5B
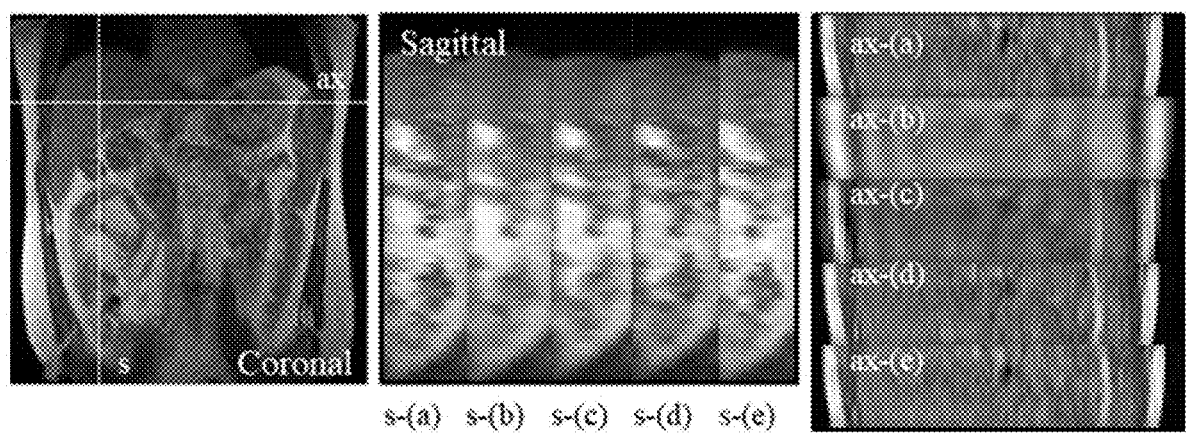
FIG. 6

METHODS AND SYSTEMS FOR REAL-TIME 3D MRI

CROSS-REFERENCE TO RELATED APPLICATIONS

This application claims priority from U.S. Provisional Application Ser. No. 62/815,194 filed on 2019 Mar. 7 and U.S. Provisional Application Ser. No. 62/880,210 filed on 2019 Jul. 30 which are incorporated herein by reference in their entireties.

STATEMENT REGARDING FEDERALLY SPONSORED RESEARCH OR DEVELOPMENT

Not applicable.

MATERIAL INCORPORATED-BY-REFERENCE

Not applicable

FIELD OF THE INVENTION

The present disclosure generally relates to methods for real-time 3D magnetic resonance imaging.

SUMMARY OF THE INVENTION

Among the various aspects of the present disclosure is the provision of methods and systems for real-time 3D MRI.

In one aspect, a computer-aided method of generating a real-time 3D magnetic resonance (MR) image of a subject is provided. The method includes obtaining a keyhole 3D MR image of the subject. The keyhole 3D MR image includes a k-space central dataset. The method also includes transforming the keyhole 3D MR image into a super-resolution 3D MR image using a deep-learning super-resolution generative (SRG) model. The method additionally includes extracting a respiratory phase of the super-resolution 3D MR image and combining an SR k-space central dataset corresponding to the super-resolution 3D MR image with a respiratory phase-matched k-space peripheral dataset retrieved from a stored library of k-space peripheral datasets to produce a combined k-space dataset. The method further includes reconstructing the real-time 3D MR image from the combined k-space dataset.

In another aspect, a computer-implemented method of treating a subject in need is provided. The method includes generating real-time 3D MR images of the subject by obtaining a keyhole 3D MR image of the subject and transforming the keyhole 3D MR image into a super-resolution 3D MR image using a deep-learning super-resolution generative (SRG) model. The keyhole 3D MR image includes a k-space central dataset. The method also includes extracting a respiratory phase of the super-resolution 3D MR image and combining an SR k-space central dataset corresponding to the super-resolution 3D MR image with a respiratory phase-matched k-space peripheral dataset retrieved from a stored library of k-space peripheral datasets to produce a combined k-space dataset. The method additionally includes reconstructing the real-time 3D MR image from the combined k-space dataset. The method further includes managing motion of a subject or a tumor in the subject using the generated real-time 3D MR images and/or gating a treatment of a subject or a tumor in the subject using the real-time 3D MR images, and any combination thereof.

In an additional aspect, a system for generating a real-time 3D MR image of a subject is provided. The system includes a computing device comprising at least one processor in which the at least one processor is configured to obtain a keyhole 3D MR image of the subject, that includes a k-space central dataset. The at least one processor is also configured to transform the keyhole 3D MR image into a super-resolution 3D MR image using a deep-learning super-resolution generative (SRG) model and to extract a respiratory phase of the super-resolution 3D MR image. The at least one processor is additionally configured to combine an SR k-space central dataset corresponding to the super-resolution 3D MR image with a respiratory phase-matched k-space peripheral dataset retrieved from a stored library of k-space peripheral datasets to produce a combined k-space dataset. The at least one processor is further configured to reconstruct the real-time 3D MR image from the combined k-space dataset.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 5A contains a series of low-spatial resolution (LR) imaging data that includes an image matrix: 64×64×10, spatial resolution: 6×6×6 mm$^3$, acquisition time: 420 ms/volume.

FIG. 5B contains a series of high-spatial resolution (LR) imaging data transformed from the low-spatial resolution (LR) imaging data of FIG. 5A using the disclosed cascaded deep learning framework. The high-spatial resolution (HR) MR imaging data includes image matrix: 256×256×10, spatial resolution: 1.5×1.5×6 mm$^3$. The generated high-spatial, high-temporal resolution prior images were inverse Fourier transformed and used in the disclosed 3D dynamic keyhole imaging. Labels I-VI indicate human subject numbers.

FIG. 6 contains a series of sagittal and axial images. Image planes (ax and s) are indicated on the coronal (left) image. The center and left images are composites comparing images obtained using various methods: (a) original image, (b) zero-filling, (c) conventional keyhole with low-spatial resolution prior data (LR_cKeyhole), (d) conventional keyhole with super-spatial resolution prior data (SR_cKeyhole), and (e) dynamic keyhole with super-spatial resolution prior data (SR_dKeyhole). On the images, s indicates sagittal imaging plane and ax indicates axial imaging plane.

DETAILED DESCRIPTION OF THE INVENTION

Figures 1A, 1B, 1C:
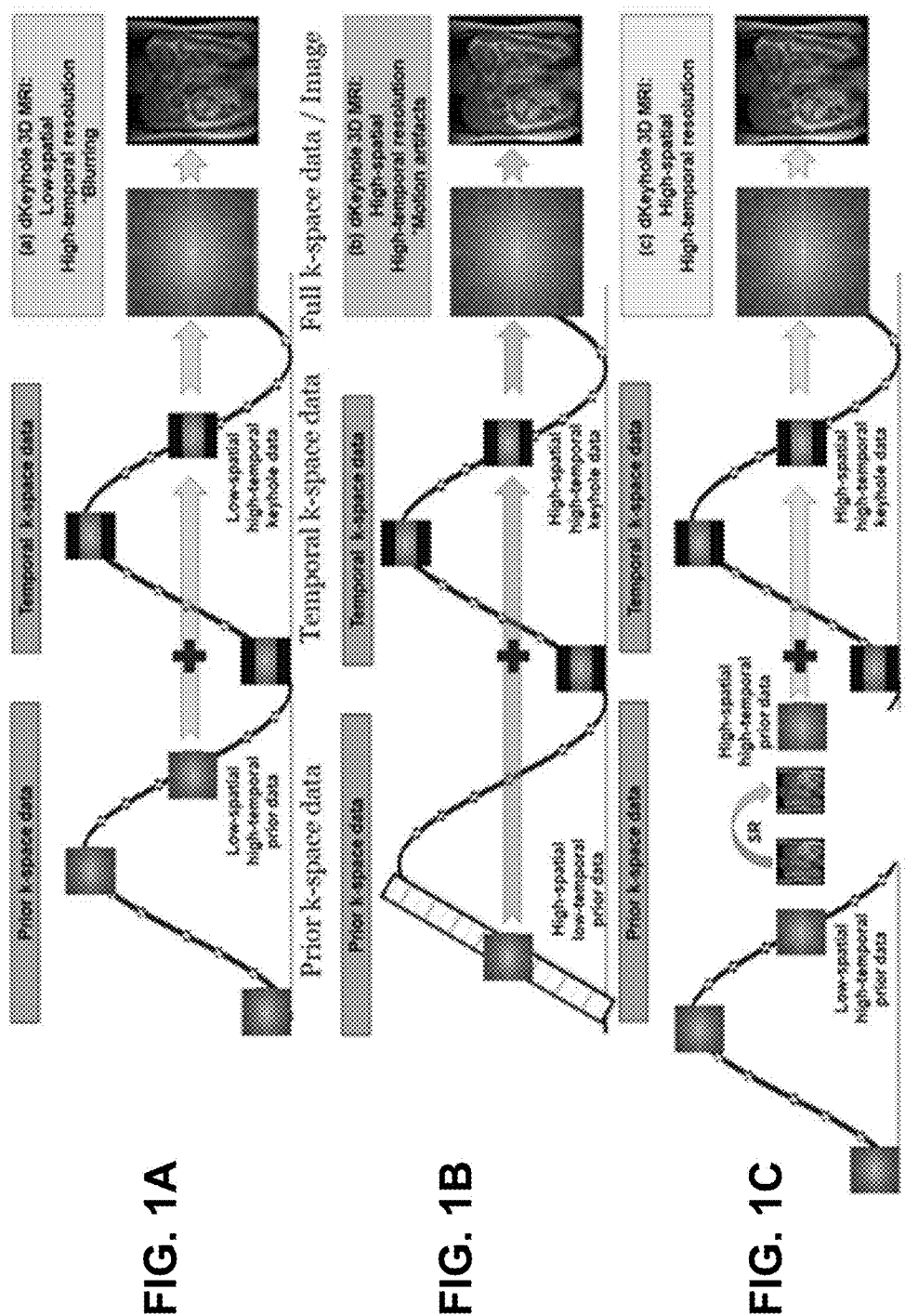
FIG. 1A is a schematic diagram of dynamic keyhole imaging for 3D MRI showing conventional 3D image acquisition in the presence of motion using low-spatial high-temporal resolution imaging that is typically available. The spatial resolution of the temporal images is determined by the spatial resolution of the preceding data in the dynamic keyhole imaging.
FIG. 1B is a schematic diagram of dynamic keyhole imaging for 3D MRI using high-spatial low-temporal resolution preceding data that is inadequate for high-spatial high-temporal resolution imaging. This approach of high-spatial high-temporal resolution imaging is deficient in conventional 3D imaging techniques (or methods) including dynamic keyhole imaging.
FIG. 1C is a schematic diagram of dynamic keyhole imaging for 3D MRI in which high-spatial, high-temporal prior data generated from low-spatial, high-temporal prior data by deep learning is used for the high-spatial, high-temporal 3D dynamic keyhole imaging.

The present disclosure is based, at least in part, on the discovery that dynamic keyhole imaging method in combination with super-resolution image reconstruction methods can improve real-time 3D MR images in the presence of motion.

Real-Time 3D MRI

One aspect of the present disclosure provides for real-time 3D MRI using Dynamic Keyhole and Super-resolution techniques or methods. Real-time high-resolution 3D MRI is highly demanded in MRI-guided radiotherapy and diagnostic MRI in the presence of motion. Existing methods of high-resolution 3D MR imaging are not well-suited for real-time high-resolution 3D MRI. High-resolution 3D MRI acquires large image matrices resolution 3D MRI that is accompanied by long data acquisition times. 3D MRI methods that make use of sparse data acquisition (i.e. a small image matrix) typically uses a time-consuming iterative reconstruction method.

In the conventional data sharing techniques or methods, such as keyhole imaging, high-temporal resolution imaging has been accomplished by reducing the amount of data acquisition associated with high-spatial resolution imaging by utilizing preceding data in image reconstruction. For instance, central k-space data contain the majority of the image information and peripheral k-space data are associated with image details such as image sharpness and edge contrast that are not necessarily specific to an individual image. Therefore, the preceding peripheral k-space data can be reused for high-temporal image acquisition without substantial image degradation, and the spatial resolution of the rapidly-acquired temporal images is enhanced by the high spatial resolution of the preceding images.

Anatomical motion information in the preceding data is another factor influencing image quality because the combined temporal and preceding image data combined in the presence of an anatomical motion mismatch can cause motion-related image artifacts. By utilizing anatomical motion information such as respiratory displacement to better match the combination of the temporal and preceding image data, the motion-related image artifacts are substantially reduced in keyhole imaging. In various aspects, dynamic keyhole imaging refers to a method of combining low-resolution temporal image datasets with preceding image data matched to the respiratory phases of each temporal image dataset. The disclosed dynamic keyhole imaging method utilizes a stored library of respiratory phase-indexed preceding peripheral k-space datasets in combination with temporal central k-space datasets acquired in real time from the subject. The preceding peripheral k-space datasets and temporal central k-space datasets are matched based on respiratory displacement, resulting in reduced MR data acquisition time and improved image quality in the presence of motion.

In MRI-guided radiotherapy and interventional MRI, high-spatial high-temporal resolution 3D image acquisition is a substantial challenge in the presence of motion because of the large imaging matrix and corresponding a long acquisition time accompanying this imaging method. Typically low-spatial high-temporal resolution imaging methods are used in practice due to the lower MR data acquisition times. Since the spatial resolution of the temporal images is determined by the spatial resolution of the preceding data in the dynamic keyhole imaging, the high-spatial low-temporal resolution preceding data is inadequate for use by the high-spatial high-temporal resolution imaging method illustrated in FIGS. 1A and 1B. Existing approaches of high-spatial high-temporal resolution imaging that are used for 2D MR imaging are deficient when extended to 3D imaging techniques or methods.

In various aspects, a real-time 3D MRI technique or method is disclosed that utilizes a data sharing method (3D dynamic keyhole) and a machine learning technique/method (super-resolution). In the disclosed method, the 3D dynamic keyhole algorithm utilizes a data sharing mechanism that combines temporal data acquired in real time with high-resolution prior templates at various motion positions prepared by the super-resolution technique/method. Since about 10% of the high-resolution data acquisition times and no additional computation time are needed to implement the disclosed real-time 3D MRI technique, real-time high-resolution 3D MRI is achieved.

This disclosure provides for a unique real-time 3D MRI method in the presence of motion by utilizing a deep learning technique (super-resolution) for high-spatial image reconstruction and a data sharing technique (3D dynamic keyhole) for high-temporal image acquisition. The disclosed real-time 3D MRI method combines two image processing elements. Super-resolution reconstruction using deep learning is used to synthesize high-spatial high-temporal resolution preceding images from low-spatial high-temporal resolution image data. Further, a 3D dynamic keyhole data sharing technique uses a library of prior peripheral k-space datasets synthesized by the deep learning, each corresponding to a different respiratory displacement to enhance the spatial resolution of the temporal MR imaging data acquired in real time. The 3D dynamic keyhole technique selects and closely matches peripheral k-space datasets from the stored library with the central k-space datasets obtained in real time.

K-space refers to a data matrix containing the raw MRI data. This data is subjected to mathematical function or formula called a transform to generate the final image.

Computing Systems and Devices

Figure 9:
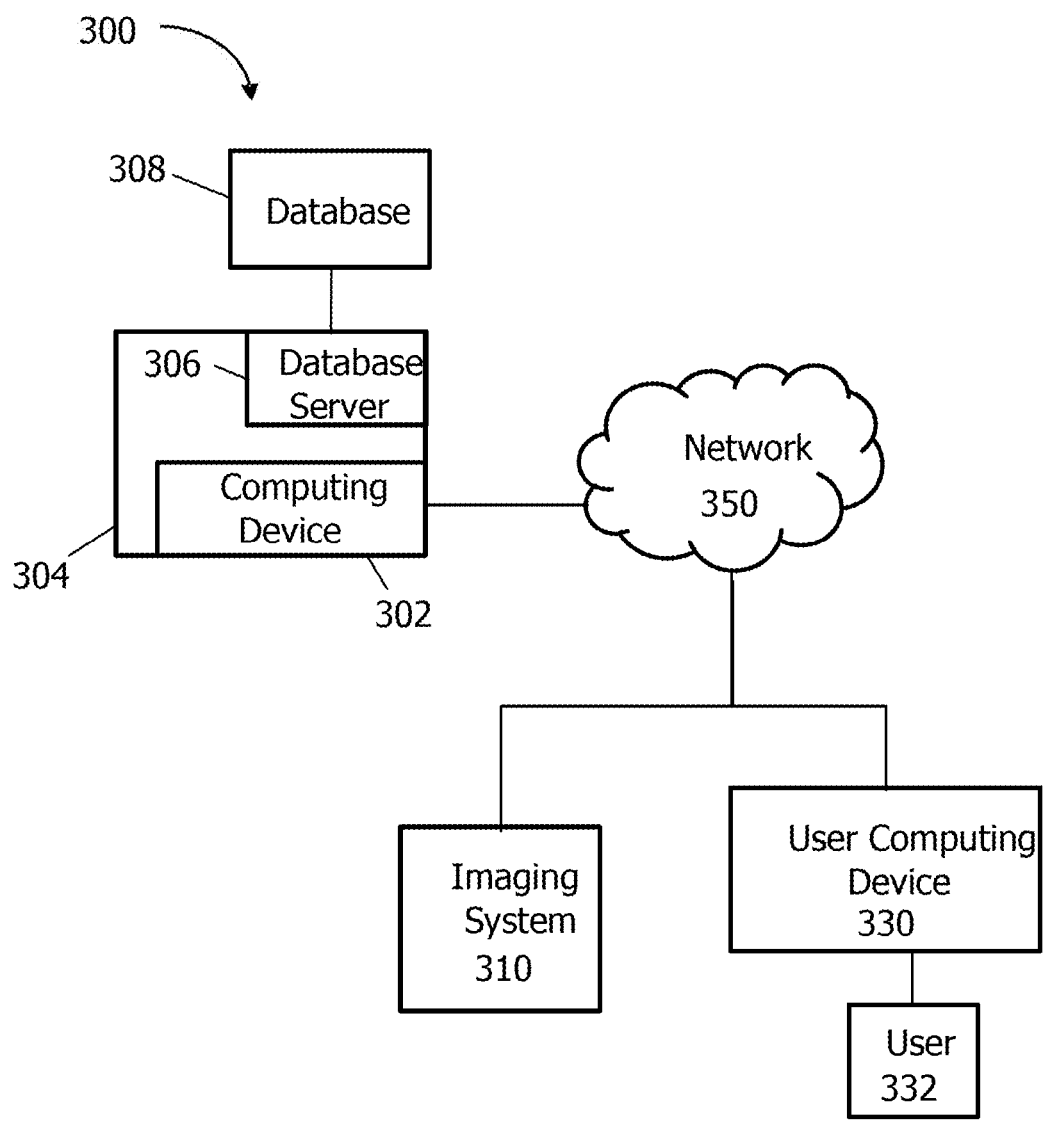
FIG. 9 is a block diagram schematically illustrating a system in accordance with one aspect of the disclosure.

FIG. 9 depicts a simplified block diagram of a computing device 300 for implementing the methods described herein. As illustrated in FIG. 9, the computing device 300 may be configured to implement at least a portion of the tasks associated with disclosed method using the system 310 including, but not limited to: operating the system to produce high-resolution MR images of a subject in real-time. The computer system 300 may include a computing device 302. In one aspect, the computing device 302 is part of a server system 304, which also includes a database server 306. The computing device 302 is in communication with a database 308 through the database server 306. The computing device 302 is communicably coupled to an imaging system 310 including, but not limited to, an MRI scanner, and is also communicably coupled to a user computing device 330 through a network 350. The network 350 may be any network that allows local area or wide area communication between the devices. For example, the network 350 may allow communicative coupling to the Internet through at least one of many interfaces including, but not limited to, at least one of a network, such as the Internet, a local area network (LAN), a wide area network (WAN), an integrated services digital network (ISDN), a dial-up-connection, a digital subscriber line (DSL), a cellular phone connection, and a cable modem. The user computing device 330 may be any device capable of accessing the Internet including, but not limited to, a desktop computer, a laptop computer, a personal digital assistant (PDA), a cellular phone, a smartphone, a tablet, a phablet, wearable electronics, smart watch, or other web-based connectable equipment or mobile devices.

Figure 10:
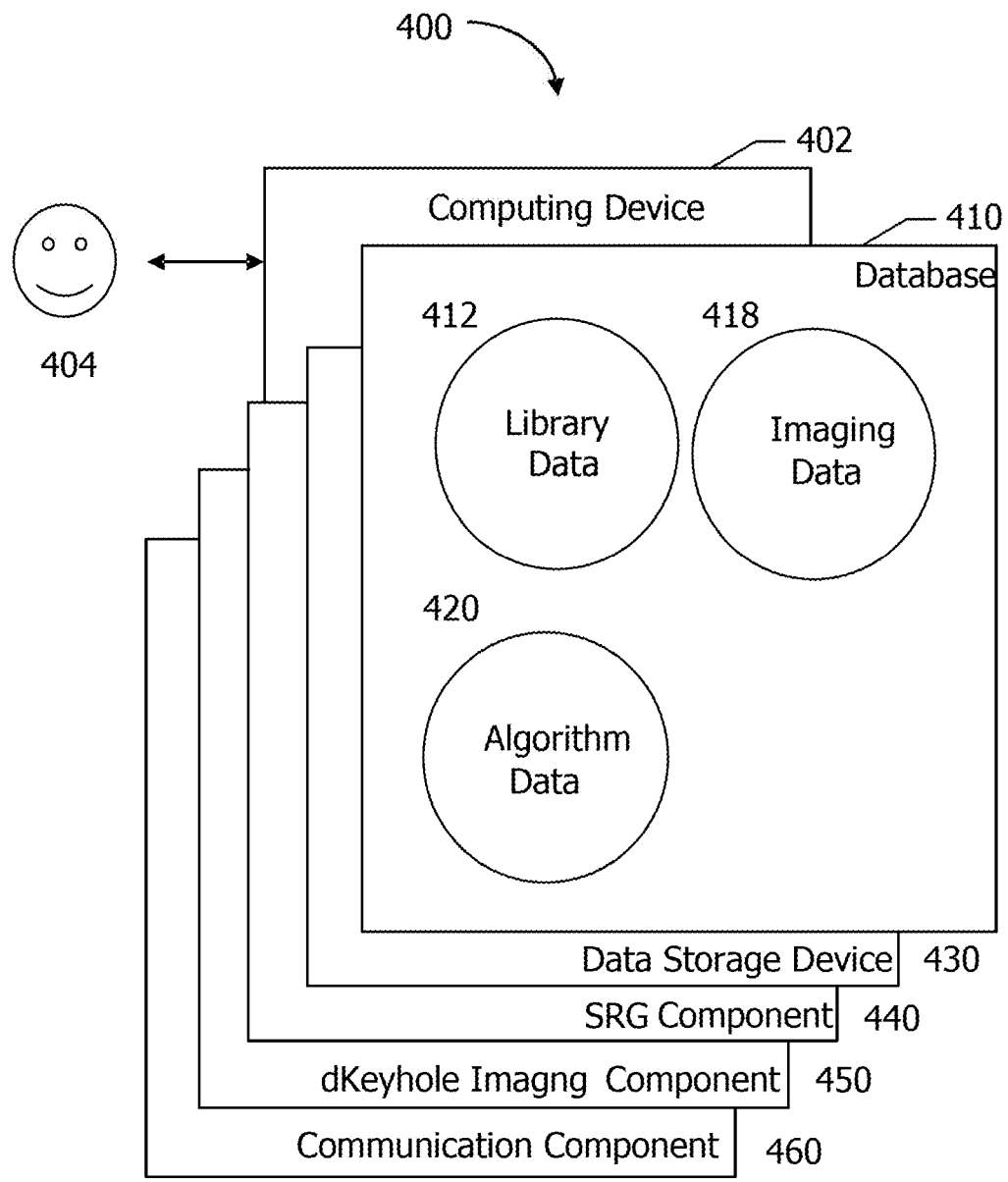
FIG. 10 is a block diagram schematically illustrating a computing device in accordance with one aspect of the disclosure.

In other aspects, the computing device 302 is configured to perform a plurality of tasks associated with produce high-resolution MR images of a subject in real-time. FIG. 10 depicts a component configuration 400 of computing device 402, which includes database 410 along with other related computing components. In some aspects, computing device 402 is similar to computing device 302 (shown in FIG. 9). A user 404 may access components of computing device 402. In some aspects, database 410 is similar to database 308 (shown in FIG. 9).

In one aspect, database 410 includes imaging data 418, algorithm data 420 defining the super-resolution generative (SRG) deep learning model and/or the denoising autoencoder (DAE) convolutional neural network (CNN), and library data 412 defining the preceding imaging data containing the respiratory phase-indexed k-space peripheral imaging. Non-limiting examples of suitable algorithm data 420 includes any values of parameters defining super-resolution generative (SRG) deep learning model and/or the denoising autoencoder (DAE) convolutional neural network (CNN). In one aspect, the library data 412 may be used to enhance the spatial resolution of the low-resolution temporal 3D MR imaging data acquired in real-time using the dynamic keyhole data sharing techniques, as described herein.

Computing device 402 also includes a number of components which perform specific tasks. In the example aspect, computing device 402 includes data storage device 430, SRG component 440, dKeyhole imaging component 450, and communication component 460. Data storage device 430 is configured to store data received or generated by computing device 402, such as any of the data stored in database 410 or any outputs of processes implemented by any component of computing device 402. SRG component 440 is configured to transform each low-resolution keyhole image acquired in real time using the SRG deep-learning model to produce a super-resolution keyhole image using the method described herein in various aspects. dKeyhole imaging component 450 is configured to combine the k-space central dataset from the super-resolution keyhole image with the respiratory phase-matched k-space peripheral data from the library data 412 and to reconstruct the combined k-space data to produce the high resolution MR image in real-time.

Communication component 460 is configured to enable communications between computing device 402 and other devices (e.g. user computing device 330 and imaging system 310, shown in FIG. 9) over a network, such as network 350 (shown in FIG. 9), or a plurality of network connections using predefined network protocols such as TCP/IP (Transmission Control Protocol/Internet Protocol).

Figure 11:
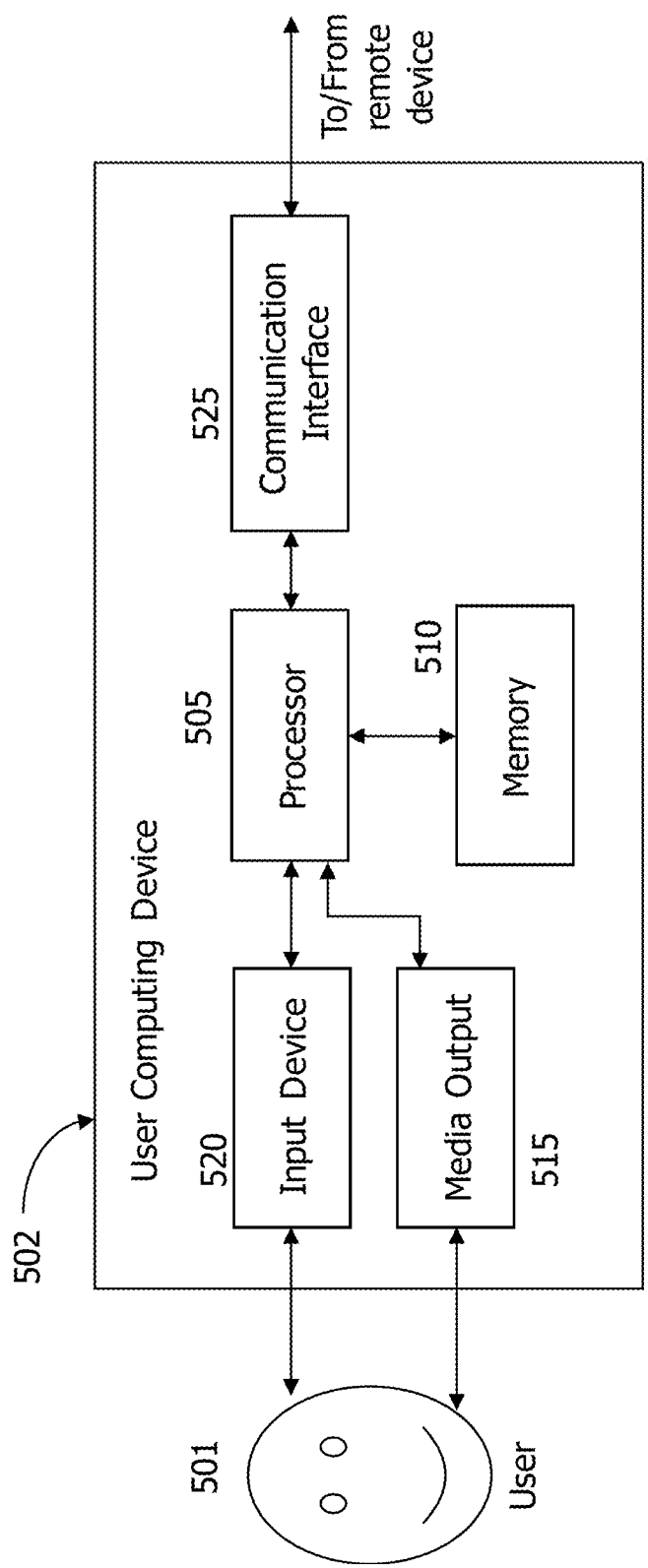
FIG. 11 is a block diagram schematically illustrating a remote or user computing device in accordance with one aspect of the disclosure.

FIG. 11 depicts a configuration of a remote or user computing device 502, such as user computing device 330 (shown in FIG. 9). Computing device 502 may include a processor 505 for executing instructions. In some aspects, executable instructions may be stored in a memory area 510. Processor 505 may include one or more processing units (e.g., in a multi-core configuration). Memory area 510 may be any device allowing information such as executable instructions and/or other data to be stored and retrieved. Memory area 510 may include one or more computer-readable media.

Computing device 502 may also include at least one media output component 515 for presenting information to a user 501. Media output component 515 may be any component capable of conveying information to user 501. In some aspects, media output component 515 may include an output adapter, such as a video adapter and/or an audio adapter. An output adapter may be operatively coupled to processor 505 and operatively coupleable to an output device such as a display device (e.g., a liquid crystal display (LCD), organic light emitting diode (OLED) display, cathode ray tube (CRT), or "electronic ink" display) or an audio output device (e.g., a speaker or headphones). In some aspects, media output component 515 may be configured to present an interactive user interface (e.g., a web browser or client application) to user 501.

In some aspects, computing device 502 may include an input device 520 for receiving input from user 501. Input device 520 may include, for example, a keyboard, a pointing device, a mouse, a stylus, a touch sensitive panel (e.g., a touch pad or a touch screen), a camera, a gyroscope, an accelerometer, a position detector, and/or an audio input device. A single component such as a touch screen may function as both an output device of media output component 515 and input device 520.

Computing device 502 may also include a communication interface 525, which may be communicatively coupleable to a remote device. Communication interface 525 may include, for example, a wired or wireless network adapter or a wireless data transceiver for use with a mobile phone network (e.g., Global System for Mobile communications (GSM), 3G, 4G or Bluetooth) or other mobile data network (e.g., Worldwide Interoperability for Microwave Access (WI MAX)).

Stored in memory area 510 are, for example, computer-readable instructions for providing a user interface to user 501 via media output component 515 and, optionally, receiving and processing input from input device 520. A user interface may include, among other possibilities, a web browser and client application. Web browsers enable users 501 to display and interact with media and other information typically embedded on a web page or a website from a web server. A client application allows users 501 to interact with a server application associated with, for example, a vendor or business.

Figure 12:
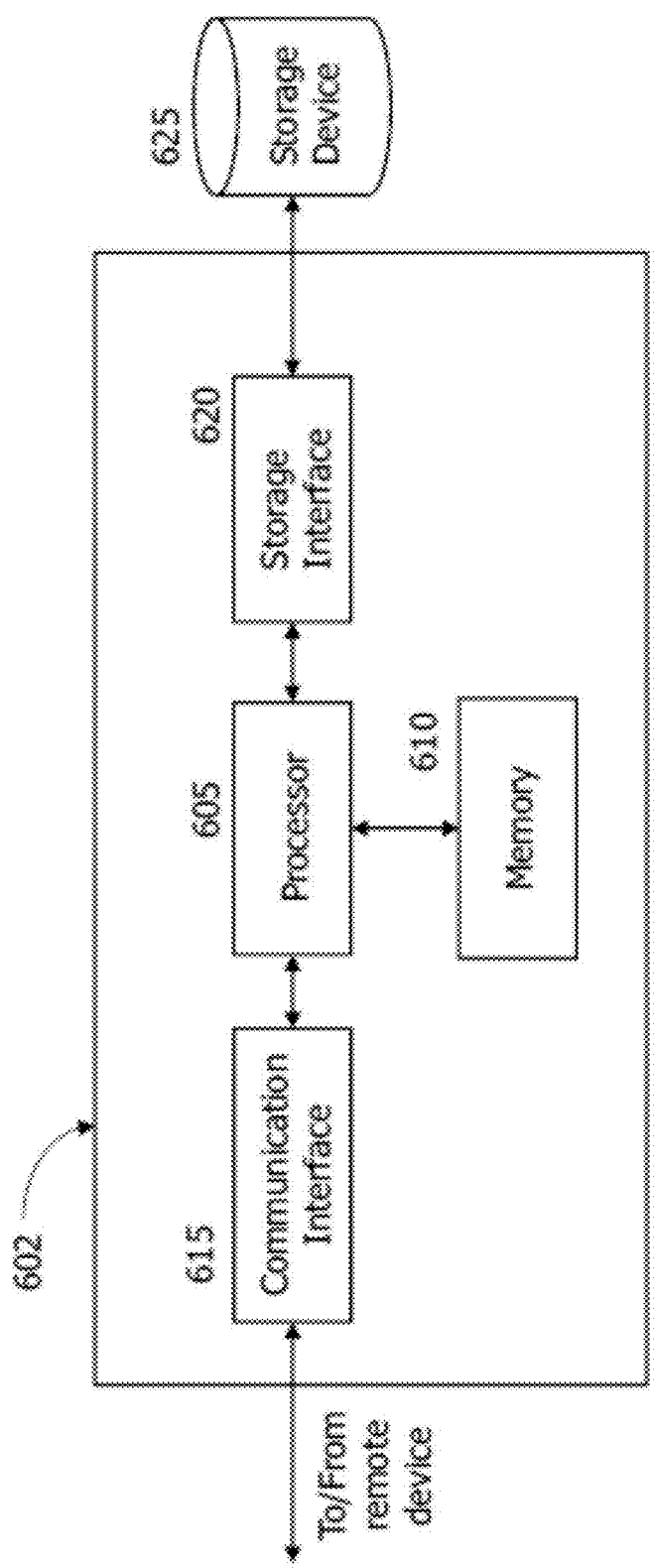
FIG. 12 is a block diagram schematically illustrating a server system in accordance with one aspect of the disclosure.

FIG. 12 illustrates an example configuration of a server system 602. Server system 602 may include, but is not limited to, database server 306 and computing device 302 (both shown in FIG. 9). In some aspects, server system 602 is similar to server system 304 (shown in FIG. 9). Server system 602 may include a processor 605 for executing instructions. Instructions may be stored in a memory area 625, for example. Processor 605 may include one or more processing units (e.g., in a multi-core configuration).

Processor 605 may be operatively coupled to a communication interface 615 such that server system 602 may be capable of communicating with a remote device such as user computing device 330 (shown in FIG. 9) or another server system 602. For example, communication interface 615 may receive requests from user computing device 330 via a network 350 (shown in FIG. 9).

Processor 605 may also be operatively coupled to a storage device 625. Storage device 625 may be any computer-operated hardware suitable for storing and/or retrieving data. In some aspects, storage device 625 may be integrated in server system 602. For example, server system 602 may include one or more hard disk drives as storage device 625. In other aspects, storage device 625 may be external to server system 602 and may be accessed by a plurality of server systems 602. For example, storage device 625 may include multiple storage units such as hard disks or solid state disks in a redundant array of inexpensive disks (RAID) configuration. Storage device 625 may include a storage area network (SAN) and/or a network attached storage (NAS) system.

In some aspects, processor 605 may be operatively coupled to storage device 625 via a storage interface 620. Storage interface 620 may be any component capable of providing processor 605 with access to storage device 625. Storage interface 620 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 605 with access to storage device 625.

Memory areas 510 (shown in FIG. 11) and 610 may include, but are not limited to, random access memory (RAM) such as dynamic RAM (DRAM) or static RAM (SRAM), read-only memory (ROM), erasable programmable read-only memory (EPROM), electrically erasable programmable read-only memory (EEPROM), and non-volatile RAM (NVRAM). The above memory types are example only, and are thus not limiting as to the types of memory usable for storage of a computer program.

The computer systems and computer-implemented methods discussed herein may include additional, less, or alternate actions and/or functionalities, including those discussed elsewhere herein. The computer systems may include or be implemented via computer-executable instructions stored on non-transitory computer-readable media. The methods may be implemented via one or more local or remote processors, transceivers, servers, and/or sensors (such as processors, transceivers, servers, and/or sensors mounted on vehicle or mobile devices, or associated with smart infrastructure or remote servers), and/or via computer executable instructions stored on non-transitory computer-readable media or medium.

In some aspects, a computing device is configured to implement machine learning, such that the computing device "learns" to analyze, organize, and/or process data without being explicitly programmed. Machine learning may be implemented through machine learning (ML) methods and algorithms. In one aspect, a machine learning (ML) module is configured to implement ML methods and algorithms. In some aspects, ML methods and algorithms are applied to data inputs and generate machine learning (ML) outputs. Data inputs may include but are not limited to: images or frames of a video, object characteristics, and object categorizations. Data inputs may further include: sensor data, image data, video data, telematics data, authentication data, authorization data, security data, mobile device data, geolocation information, transaction data, personal identification data, financial data, usage data, weather pattern data, "big data" sets, and/or user preference data. ML outputs may include but are not limited to: a tracked shape output, categorization of an object, categorization of a type of motion, a diagnosis based on motion of an object, motion analysis of an object, and trained model parameters ML outputs may further include: speech recognition, image or video recognition, medical diagnoses, statistical or financial models, autonomous vehicle decision-making models, robotics behavior modeling, fraud detection analysis, user recommendations and personalization, game AI, skill acquisition, targeted marketing, big data visualization, weather forecasting, and/or information extracted about a computer device, a user, a home, a vehicle, or a party of a transaction. In some aspects, data inputs may include certain ML outputs.

In some aspects, at least one of a plurality of ML methods and algorithms may be applied, which may include but are not limited to: linear or logistic regression, instance-based algorithms, regularization algorithms, decision trees, Bayesian networks, cluster analysis, association rule learning, artificial neural networks, deep learning, dimensionality reduction, and support vector machines. In various aspects, the implemented ML methods and algorithms are directed toward at least one of a plurality of categorizations of machine learning, such as supervised learning, unsupervised learning, and reinforcement learning.

In one aspect, ML methods and algorithms are directed toward supervised learning, which involves identifying patterns in existing data to make predictions about subsequently received data. Specifically, ML methods and algorithms directed toward supervised learning are "trained" through training data, which includes example inputs and associated example outputs. Based on the training data, the ML methods and algorithms may generate a predictive function which maps outputs to inputs and utilize the predictive function to generate ML outputs based on data inputs. The example inputs and example outputs of the training data may include any of the data inputs or ML outputs described above.

In another aspect, ML methods and algorithms are directed toward unsupervised learning, which involves finding meaningful relationships in unorganized data. Unlike supervised learning, unsupervised learning does not involve user-initiated training based on example inputs with associated outputs. Rather, in unsupervised learning, unlabeled data, which may be any combination of data inputs and/or ML outputs as described above, is organized according to an algorithm-determined relationship.

In yet another aspect, ML methods and algorithms are directed toward reinforcement learning, which involves optimizing outputs based on feedback from a reward signal. Specifically ML methods and algorithms directed toward reinforcement learning may receive a user-defined reward signal definition, receive a data input, utilize a decision-making model to generate a ML output based on the data input, receive a reward signal based on the reward signal definition and the ML output, and alter the decision-making model so as to receive a stronger reward signal for subsequently generated ML outputs. The reward signal definition may be based on any of the data inputs or ML outputs described above. In one aspect, a ML module implements reinforcement learning in a user recommendation application. The ML module may utilize a decision-making model to generate a ranked list of options based on user information received from the user and may further receive selection data based on a user selection of one of the ranked options. A reward signal may be generated based on comparing the selection data to the ranking of the selected option. The ML module may update the decision-making model such that subsequently generated rankings more accurately predict a user selection.

As will be appreciated based upon the foregoing specification, the above-described aspects of the disclosure may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the discussed aspects of the disclosure. The computer-readable media may be, for example, but is not limited to, a fixed (hard) drive, diskette, optical disk, magnetic tape, semiconductor memory such as read-only memory (ROM), and/or any transmitting/receiving medium, such as the Internet or other communication network or link. The article of manufacture containing the computer code may be made and/or used by executing the code directly from one medium, by copying the code from one medium to another medium, or by transmitting the code over a network.

These computer programs (also known as programs, software, software applications, "apps", or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The "machine-readable medium" and "computer-readable medium," however, do not include transitory signals. The term "machine-readable signal" refers to any signal used to provide machine instructions and/or data to a programmable processor.

As used herein, a processor may include any programmable system including systems using micro-controllers, reduced instruction set circuits (RISC), application specific integrated circuits (ASICs), logic circuits, and any other circuit or processor capable of executing the functions described herein. The above examples are example only, and are thus not intended to limit in any way the definition and/or meaning of the term "processor."

As used herein, the terms "software" and "firmware" are interchangeable, and include any computer program stored in memory for execution by a processor, including RAM memory, ROM memory, EPROM memory, EEPROM memory, and non-volatile RAM (NVRAM) memory. The above memory types are example only, and are thus not limiting as to the types of memory usable for storage of a computer program.

In one aspect, a computer program is provided, and the program is embodied on a computer readable medium. In one aspect, the system is executed on a single computer system, without requiring a connection to a sever computer. In a further aspect, the system is being run in a Windows® environment (Windows is a registered trademark of Microsoft Corporation, Redmond, Wash.). In yet another aspect, the system is run on a mainframe environment and a UNIX® server environment (UNIX is a registered trademark of X/Open Company Limited located in Reading, Berkshire, United Kingdom). The application is flexible and designed to run in various different environments without compromising any major functionality.

In some aspects, the system includes multiple components distributed among a plurality of computing devices. One or more components may be in the form of computer-executable instructions embodied in a computer-readable medium. The systems and processes are not limited to the specific aspects described herein. In addition, components of each system and each process can be practiced independent and separate from other components and processes described herein. Each component and process can also be used in combination with other assembly packages and processes. The present aspects may enhance the functionality and functioning of computers and/or computer systems.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as length of time, pulse sequence parameters, experimental parameters or conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Real-Time 3D MRI in the Presence of Motion: Dynamic Keyhole with Super-Resolution The following example describes the a unique real-time 3D MRI technique in the presence of motion by utilizing a deep learning technique (super-resolution) for high-spatial image reconstruction and a data sharing technique (3D dynamic keyhole) for high-temporal image acquisition. There are two elements in the proposed techniques. 1) Super-resolution reconstruction using deep learning synthesizes high-spatial high-temporal resolution preceding images from low-spatial high-temporal resolution ones. 2) Instead of using a single preceding data, 3D dynamic keyhole uses a library of prior peripheral k-space datasets synthesized by the deep learning, each corresponding to a different respiratory displacement. 3D dynamic keyhole selects and closely matches peripheral k-space datasets from the library, with the central k-space datasets taken in real time.

3D Dynamic Keyhole Imaging with High-Spatial High-Temporal Resolution Preceding Images Disclosed here, is a real-time high-spatial resolution 3D MRI technique in the presence of motion by utilizing a deep learning technique (super-resolution) for high-spatial image reconstruction and a data sharing technique (3D dynamic keyhole) for high-temporal image acquisition. There are two components in the disclosed techniques. 1) Super-resolution reconstruction using deep learning synthesizes high-spatial high-temporal resolution preceding images from low-spatial high-temporal resolution ones. 2) 3D dynamic keyhole uses a library of prior peripheral k-space datasets synthesized by the deep learning, each corresponding to a different respiratory displacement. 3D dynamic keyhole selects and closely matches peripheral k-space datasets from the library, with the central k-space datasets taken in real time as illustrated in FIG. 1C.

Low-Spatial High-Temporal Resolution Preceding Image Acquisition

All data used in these experiments study were acquired from a commercially available MR-IGRT system (ViewRay Inc., Oakwood Village, Ohio) that integrates a split-bore 0.35 T whole body MRI system with a three head Co-60 radiation therapy delivery system. MR images of four healthy volunteers were acquired using a torso coil. 3D images in coronal orientation were acquired using the balanced steady-state free precession (bSSFP) sequence. The generalized auto calibrating partially parallel acquisition (GRAPPA) technique was used to speed up image acquisition (iPAT=2). Imaging parameters are base resolution=64, phase partial Fourier=6/8, TR/TE=1.75/0.81 ms, voxel size=6×6×6 mm$^3$ and total acquisition time/volume=420 ms.

High-Spatial High-Temporal Resolution Image Synthesis (Super Resolution Reconstruction) Using Cascaded Deep Learning (DL)

Deep learning (DL)-based super resolution (SR) reconstruction for magnetic resonance imaging (MRI) accomplishes the significant improvement in spatial resolution compared to conventional SR techniques. Low-spatial resolution (LR) MR images captured in the clinic exhibit complex tissue structures obfuscated by noise that are difficult for a simple DL framework to handle. Moreover, training a robust network for a SR task requires abundant, perfectly matched pairs of LR and high-spatial resolution (HR) images that are often unavailable or impossible to collect. The disclosed SR technique is based on the concept of cascaded DL allows the reconstruction of high-quality SR images in the presence of insufficient training data, an unknown translation model, and noise.

Simulation Studies

The efficacy of the 3D dynamic keyhole reconstruction with super-resolution preceding images has been compared to the zero-filling reconstruction, conventional keyhole reconstruction with low-spatial high-temporal preceding data and conventional keyhole reconstruction with super-resolution preceding data. Four 4D MRI datasets from four human subjects (3D MRI with 10 slices at 20 respiratory displacements) were acquired for comparison. Respiratory displacement was extracted from the profile of diaphragm on the coronal middle slice of 3D MRI. The quality of the reconstructed images with the reduced temporal ky lines (26 of 256/slice) was compared with the original image with the full k-space dataset. Image intensity difference was used to evaluate image quality and artifacts.

Figure 2:
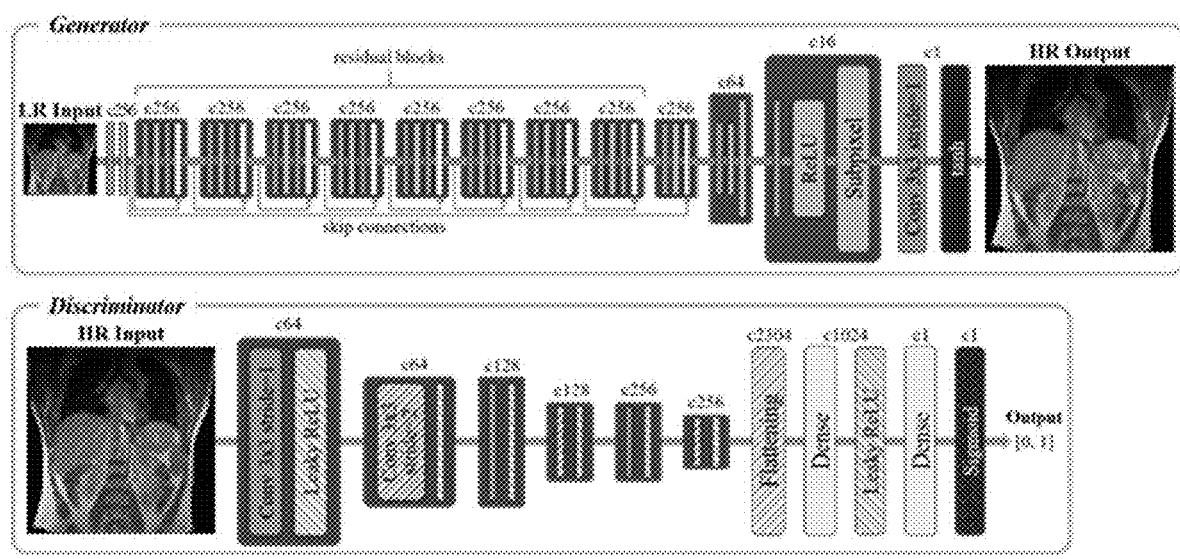
FIG. 2 shows network structures of the components of the super-resolution generative (SRG) model based on the generative adversarial network (GAN) framework. During the SRG model training, the network aims to learn the image prior for inversely mapping the low-spatial resolution image to the reference high-spatial resolution image. Specifically, a high-spatial resolution image was constructed iteratively to best explain the given data set of low-spatial resolution images by minimizing the differences between the given high-spatial resolution images and the generated high-spatial resolution version of low-spatial resolution images fed into the network through the front end De-noising auto-encoder (DAE).
Figure 3:
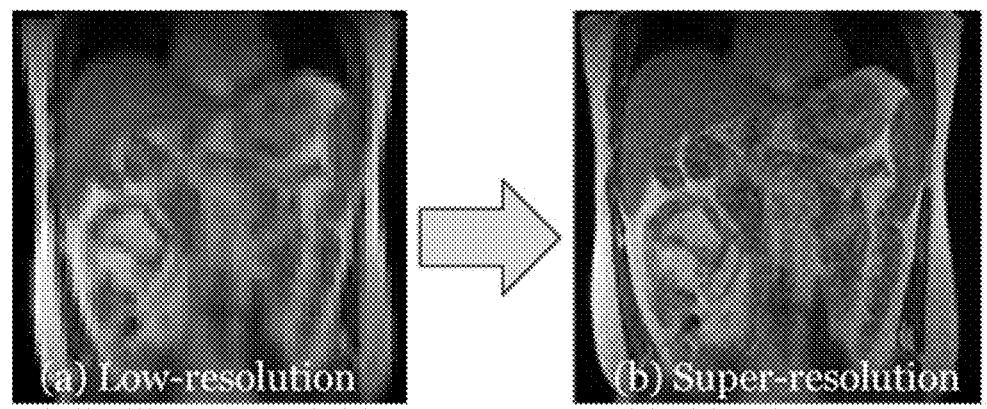
FIG. 3 illustrates the transformation of a 64×64 pixels, 6.0 mm×6.0 mm per pixel image (left) into a 256×256 pixels, 1.5 mm×1.5 mm per pixel image (right) of coronal 4D-MRI acquisition with free breathing using the cascaded deep learning framework. Synthesized super-spatial high-temporal resolution preceding images were reused in 3D dynamic keyhole imaging.

Results: High-Spatial High-Temporal Resolution Image Synthesis for 3D Dynamic Keyhole High-spatial high-temporal resolution 4D MRI (256×256 pixels, 1.5 mm×1.5 mm per pixel) was synthesized from low-spatial high-temporal resolution 4D images acquired on coronal plane (64×64 pixels, 6.0 mm×6.0 mm per pixel) by using the cascaded deep learning framework illustrated in FIG. 2. Synthesized images were assigned as high-spatial high-temporal resolution preceding data which were reused in 3D dynamic keyhole imaging. FIG. 3 shows both the low-spatial resolution (Low-resolution) and synthesized high-spatial resolution (super-resolution) MR images.

Results: High-Spatial High-Temporal Resolution 3D MRI 4 reconstruction techniques were implemented using the imaging data acquired with the reduced acquisition time (~450 ms) to produce high-spatial high-temporal resolution images that were compared with the original high-spatial resolution images (estimated acquisition time: ~4,500 ms): zero-filling, conventional keyhole with low-spatial resolution preceding data (LR_cKeyhole), conventional keyhole with super-spatial resolution preceding data (SR_cKeyhole) and dynamic keyhole with super-spatial resolution preceding data (SR_dKeyhole).

Zero-filling reconstructed blurred images due to a lack of fine image details from missing peripheral k-space data and LR_cKeyhole reconstructed blurred images due to the low-spatial resolution preceding image with unmatched motion information. SR_cKeyhole improved image quality by using high-spatial resolution preceding image but motion-related artifacts remained due to motion-phase mismatches between the keyhole data associated with different respiratory phases for each and the preceding peripheral MR data associated with a single respiratory phase. SR_dKeyhole reconstructed images most similar to the original images since it utilized high-spatial resolution preceding image with suitable motion information in data combination. Also, the difference maps of the reconstructed coronal images from the original high-spatial resolution data indicates SR_dKeyhole is the most favorable technique for real-time high-spatial resolution 3D MRI in FIG. 4. The differences of the images are displayed with an intensity range between 0 and 9000 for visual inspection. SSIM of the reconstructed 3D MRI to the original 3D MRI were 0.65, 0.66, 0.86 and 0.89 for zero-filling, LR_cKeyhole, SR_cKeyhole and SR_dKeyhole (1 for identical image). In addition, the IRE scores from comparing the reconstructed 3D MRI to the original 3D MRI were 0.169, 0.191, 0.079 and 0.067 for zero-filling, LR_cKeyhole, SR_cKeyhole and SR_dKeyhole, respectively.

FIG. 6 shows sagittal and axial images reconstructed using four techniques. Image planes are indicated on the coronal image (s: sagittal imaging plane, ax: axial imaging plane): (a) original SR image, (b) zero-filling image, (c) conventional keyhole image with low-spatial resolution prior data (LR_cKeyhole), (d) conventional keyhole image with super-spatial resolution prior data (SR_cKeyhole), and (e) dynamic keyhole image with super-spatial resolution prior data (SR_dKeyhole), respectively. Since the super-resolution was conducted in the coronal imaging plane, the anterior-posterior (AP) direction of the sagittal image and the axial image showed less distinction among four reconstructed images from the original image. According to the visual inspection, SR_dKeyhole-reconstructed images were most similar to the original SR images without any distinct artifacts.

Figure 7A:
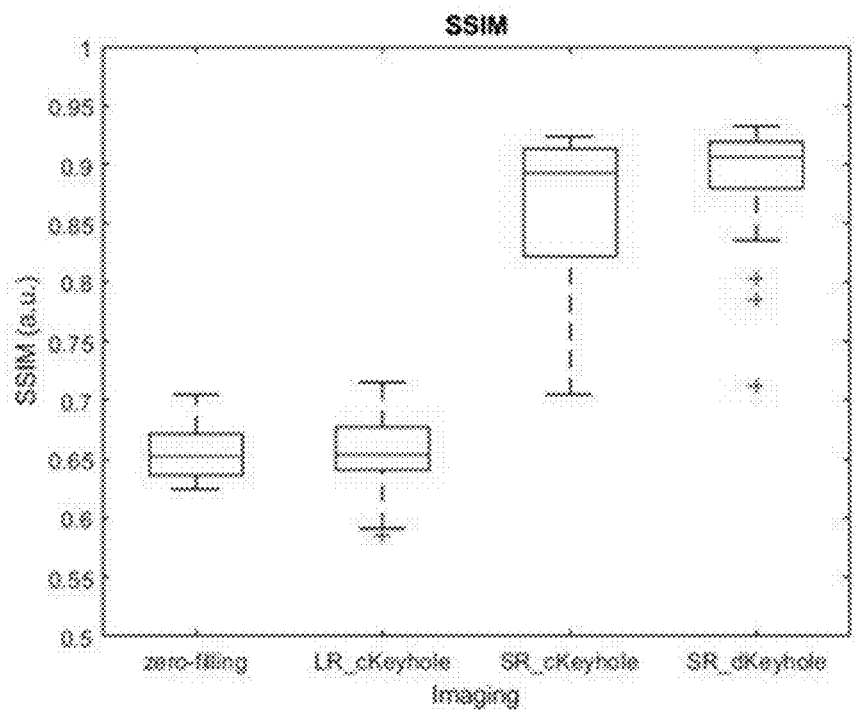
FIG. 7A is a box plot of SSIM obtained using a similarity evaluation between the original 3D images and the reconstructed 3D images with four imaging techniques. Mean values of SSIM were 0.65, 0.66, 0.86 and 0.89 for zero-filling, LR_cKeyhole, SR_cKeyhole, and SR_dKeyhole.
Figure 7B:
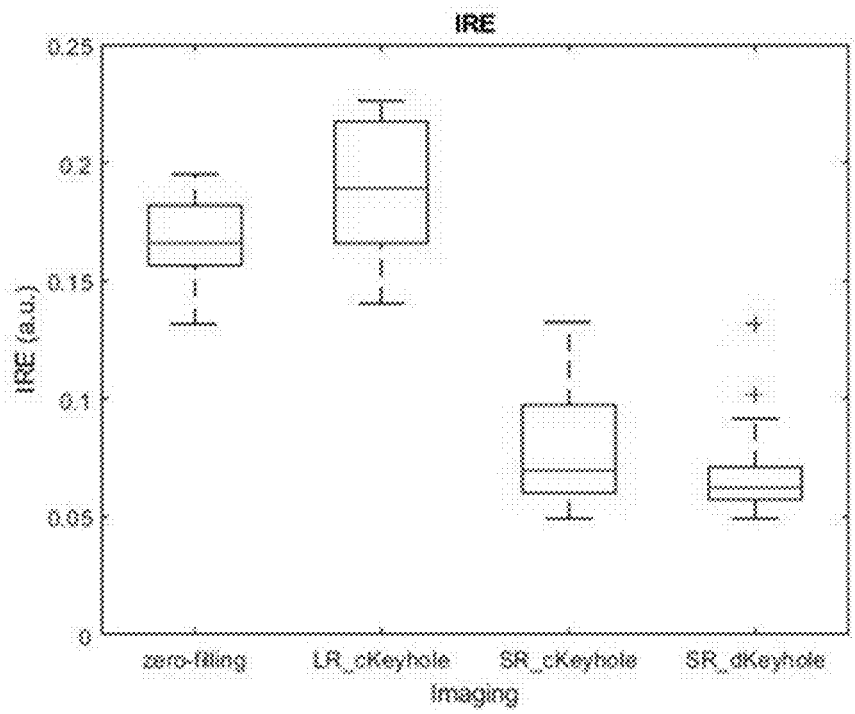
FIG. 7B is a box plot of IRE obtained using a similarity evaluation between the original 3D images and the reconstructed 3D images with four imaging techniques. In addition, mean values of IRE are 0.169, 0.191, 0.079 and 0.067 for zero-filling, LR_cKeyhole, SR_cKeyhole, and SR_dKeyhole, respectively.

SSIM and IRE measurements of image quality of the images reconstructed using the four methods of FIG. 6 are presented in FIG. 7A and FIG. 7B, respectively. In the box plot, 37 respiratory samples were included: 10 respiratory samples from each human subject I-III and 7 respiratory samples from human subject IV (due to long respiratory cycle). Reconstructed 3D images of four human subjects show different level of similarity to the original 3D MRI; SSIM mean±standard deviation were 0.65±0.02, 0.66±0.03, 0.86±0.07 and 0.89±0.05 for zero-filling, LR_cKeyhole, SR_cKeyhole, and SR_dKeyhole, respectively. In addition, IRE mean±standard deviation were 0.169±0.017, 0.191±0.025, 0.079±0.024 and 0.067±0.016 for zero-filling, LR_cKeyhole, SR_cKeyhole, and SR_dKeyhole, respectively. Reconstructed images by SR_dKeyhole show the highest similarity and the least variance to the original images, while SR_cKeyhole show the second highest similarity but the largest variance to the original images. In contrast, LR_cKeyhole images show the least similarity to the original images.

Discussion

In MR-guided radiotherapy (MRgRT), high-spatial volumetric 3D MRI is used for patient alignment and target/organ delineations. During treatment delivery, high-temporal 2D cine MRI (~5 frames/sec) or low-temporal 3D MRI (1 volume/7 seconds) is typically used for continuous patient monitoring. However, since tumors near the diaphragm exhibit 3D motion, neither 2D approach properly detects 3D tumor motion in real-time. Therefore, high-spatial, high-temporal resolution 3D MRI is highly needed in real-time MRgRT.

The examples disclosed above demonstrated high-spatial, high-temporal 3D MRI implemented by combining 3D dynamic keyhole imaging with the SRG model as described herein. High-spatial resolution images were prepared as the prior data using super-resolution prior data (<100 ms/volume) generated from low-spatial high-temporal resolution images (<1 minute for 20 volumes). 3D dynamic keyhole imaging accelerated the acquisition time by reducing the size of the keyhole data acquired in real-time, resulting in high-temporal resolution imaging. According to these findings, the disclosed high-resolution real-time MR imaging method, which uses an estimated data acquisition time of 455 ms for each 3D MR image, provided image quality close to the image quality of ground-truth super-resolution 3D MR images reconstructed with full k-space data with an estimated acquisition time of 4,480 ms. In addition, the disclosed method used the conventional Fourier-transform image reconstruction so no additional computational time and power were needed for image reconstruction, unlike iterative reconstructions of real-time 3D MRI with undersampled schemes and retrospective 4D MRI. In various other aspects, partial Fourier acquisition and/or reduced field of view approaches may also be combined with 3D dynamic keyhole to may further accelerate the 3D MRI imaging time.

In terms of the imaging time, the conventional keyhole imaging with low spatial-resolution prior data (LR_cKeyhole) is feasible without the support of the SRG model. The image quality appears better than the zero-filled reconstructed images. However, SSIM and IRE show that the image similarity of the conventional keyhole images is quite low compared to SR_cKeyhole and SR_dKeyhole, supporting the necessity of high-spatial resolution prior data in keyhole imaging. Also, the SRG model can be directly used to generate high-spatial, high-temporal 3D MRI with higher power computation support. Compared to the direct use of the SRG model, the dynamic keyhole imaging utilized higher input data fidelity, providing a simple and robust imaging method for real-time MRgRT. For example, the SRG model utilizes low-spatial resolution images (image matrix: 64×64 from k-space data matrix with 24 phase encodes using iPAT=2 and 6/8 partial Fourier). In contrast, the dynamic keyhole reconstruction uses partial high-spatial resolution central k-space data (k-space data matrix: 256× 26) in its reconstruction. In addition, the input data fidelity can be increased by updating partial high-spatial resolution peripheral k-space data through temporal data acquisition in the dynamic keyhole imaging. Therefore, higher input data fidelity is a key component of the dynamic keyhole imaging compared to the SRG model.

Figure 4:
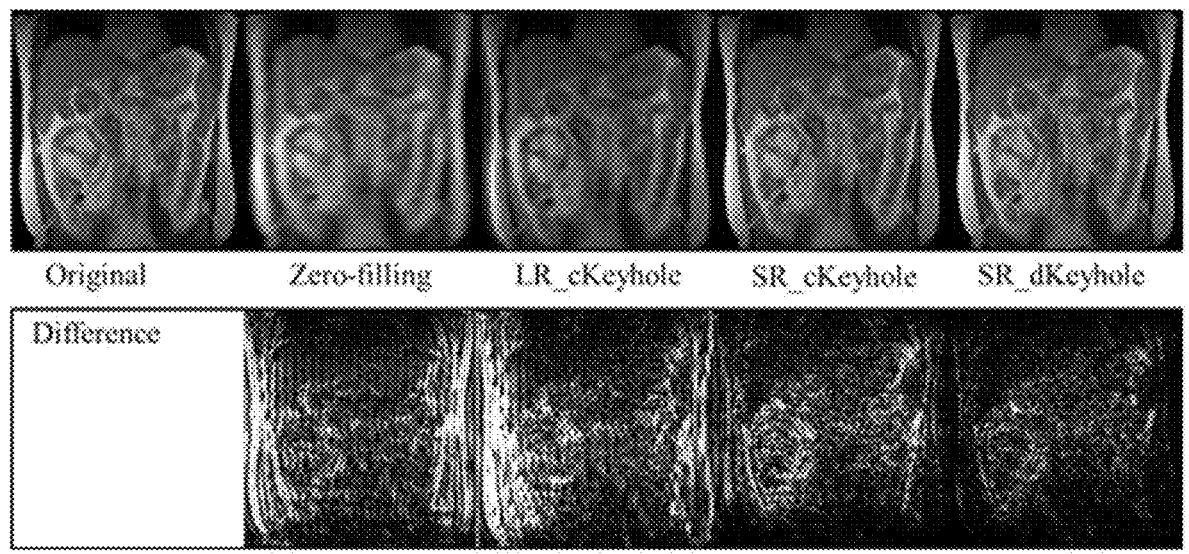
FIG. 4 contains a series of images comparing four reconstruction techniques (or methods) for real-time high-spatial 3D MRI with a reduced acquisition time (~450 ms): zero-filling, conventional keyhole with low-spatial resolution preceding data (LR_cKeyhole), conventional keyhole with super-spatial resolution preceding data (SR_cKeyhole) and dynamic keyhole with super-spatial resolution preceding data (SR_dKeyhole). The estimated acquisition time of the original high-spatial resolution 3D images is ~4,500 ms. Difference maps of the reconstructed coronal images from the original high-spatial resolution data (bottom row) indicate that SR_dKeyhole is the most favorable technique or method for real-time high-spatial 3D MRI.

By utilizing anatomical motion information such as respiratory displacement in keyhole imaging, real-time MRI in the presence of respiratory motion can be acquired without substantial motion artifacts. FIG. 4, FIG. 7A, and FIG. 7B show the limitation of the conventional keyhole imaging including distinct motion artifacts and similarity variation depending on the respiratory displacement. In FIG. 7A and FIG. 7B, the SR_dKeyhole reconstructed images with the highest similarity and the least variance relative to the original SR images. SR_cKeyhole images showed the second highest similarity but the largest variance to the original images due to uncoupling of the prior peripheral k-space data from the temporal central k-space data, thus indicating the importance of the respiratory phase information. In this simulation study, respiratory displacement was extracted from the profile of the diaphragm on the middle coronal slice of the 3D MRI. In MRI scanners, the respiratory signal can also be extracted as a 1D Fourier transform of the kx line at the ky-kz center.

In the current MRgRT workflow, there are no MRI acquisitions occurring between 3D MRI in treatment setup and 2D cine in treatment delivery because there are few treatment preparation steps: patient alignment, daily anatomy-based delineations, and plan verification. The acquisition dead-time can be used for the prior data preparation including the low-spatial, high-temporal imaging (<1 minute) and the corresponding SR images (<1 minute). Once the treatment starts, 3D dynamic keyhole imaging can be launched for real-time 3D MRgRT.

In the examples described herein, super-resolution was performed in the coronal imaging plane (in-plane: superior-inferior and left-right) and the through-plane (anterior-posterior) resolution remained (6 mm). The data reduction in 3D dynamic keyhole imaging was implemented only along ky. In various aspects, the data reduction of ky and kz in 3D dynamic keyhole imaging may also be implemented with super-resolution imaging conducted in both in-plane and through-plane.

Conclusion

This example demonstrated high-spatial, high-temporal 3D MRI was feasible by combining 3D dynamic keyhole imaging with the SRG deep-learning model. The image quality achieved using the disclosed method was similar to the original SR images with full k-space data while achieving large accelerations in acquisition time. After the library preparation, there was no additional computational time and power needed with the conventional Fourier-transform image reconstruction in 3D imaging unlike undersampled approaches. Validating and evaluating robustness of the technique are ongoing. The disclosed 3D dynamic keyhole imaging combined with the SRG model is suitable for used in real-time MRgRT methods, thus establishing a paradigm for real-time 3D imaging schemes, structure segmentation and gating algorithms.

Methods

The proposed techniques utilized two key components for high-spatial, high-temporal 3D MRI: 1) dynamic keyhole imaging for high-temporal acquisition; and 2) SRG model for high-spatial reconstruction.

Low-Spatial, High-Temporal Resolution Image Acquisition

All data used in this study were acquired from a 0.35 T MRgRT system (ViewRay Inc., Oakwood Village, Ohio) with a three head Co-60 radiation therapy delivery system. MRIs of human subjects were acquired using anterior and posterior torso phased array receive only coils. Twenty real-time volumetric 3D MRI datasets were acquired continuously (free breathing) across multiple respiratory cycles for four human subjects. 3D images in coronal orientation were acquired using the true fast imaging using steady-state precession (TrueFISP). The generalized auto calibrating partially parallel acquisition (GRAPPA) technique was used to speed up image acquisition (iPAT=2). Imaging parameters are base resolution=64, phase partial Fourier=6/8, TR/TE=1.75/0.81 ms, voxel size=6×6×6 mm$^3$ and total acquisition time/volume=420 ms.

High-Spatial, High-Temporal Resolution Prior Image Generation (Super Resolution) Using Cascaded Deep Learning The deep learning (DL)-based SR generative (SRG) model for MRI accomplishes a significant improvement in spatial resolution compared to conventional SR techniques such as interpolation-based methods. SR images can be generated without transformation models since DL-based methods utilize direct mapping based on information extracted from previous datasets. Recent studies have shown that the in-plane resolution of physically scanned low-spatial resolution 3D MRI can be improved to a four times higher resolution without compromising the image quality. A cascaded DL-based SRG model used a splitting SR generation process to make a SR model robust compared to the conventional DL-based methods. The cascaded DL-based SR consisted of three training stages: 1) training of a de-noising auto-encoder (DAE) using noise reduced low-spatial resolution data; 2) training of a down-sampling network (DSN) using a paired low-spatial resolution (LR)/high-spatial resolution (HR) data that allows the generation of perfectly paired LR/HR data from the clinically abundant HR scans; and 3) the training of a SRG trained with data generated by the DSN that maps from LR inputs to HR outputs. The training was performed using a GeForce GTX 1080 Ti GPU (NVIDIA, Santa Clara, Calif.).

1) Training of a de-noising auto-encoder (DAE): Image de-nosing is needed since SR generation is sensitive to image noise. Conventional image de-noising techniques are not efficient in processing time and computation power. In the training process, a convolutional neural network (CNN)-based DAE for high accuracy was used. The DAE was trained with pairs of noisy and de-noised LR MRIs that were preprocessed using the non-local means filter (NLM). Four hundred eighty LR breath-hold images were used in the DAE training (training time: around 35 minutes).

2) Training of a down-sampling network (DSN): After the DAE training, paired LR and HR MR images were used in the down-sampling network training. The images were scanned from a phantom and volunteers in a single breath hold. Inventors manually selected the data pairs until the HR and LR scans were perfectly paired. A CNN-based DSN was developed for the down-sampling process using 480 data pairs of LR and HR images. In the training, inventors ensured that the resulting LR images were similar to the ground-truth LR images from the scanner. HR MR images of 256×256 pixels (1.5×1.5 mm) and the corresponding LR images of 64×64 pixels (6.0×6.0 mm) were used in the testing and inferencing steps (training time: around 20 minutes).

3) Training of SRG model: The robustness of the DSN was a key component in the performance of the SRG model because the DNS was used to generate LR MRIs for the SRG model training. The SRG network was then trained with 4,475 data pairs from the set of axial LR MRIs to create axial SR MRIs and 1,375 data pairs from LR 4D MRIs to create SR 4D MRIs, respectively. The data pairs consisted of clinically available HR MR images and the corresponding LR images generated by the DSN. In the training, inventors verified the SRG model with fast axial MRI in a breath-hold and multi-volumetric cine 3D MRI. The axial SR MRIs were generated from the set of axial LR MRIs acquired in a short breath-hold interval (<3 sec). SR multi-volumetric cine 3D MRIs were generated from multi-volumetric LR cine 3D MRI acquired at rate of 2 volumes/sec (training time: around 4 hours 15 minutes).

After the verification of DL-based SRG model, inventors generated the SR multi-volumetric cine 3D MRIs from LR MRIs using the SRG model (twenty SR volumetric cine 3D MRI datasets/each human subject). In this study, inventors utilized the pairs of the SR multi-volumetric cine 3D MRI and the LR multi-volumetric cine 3D MRI. The SR MRIs were used as the ground-truth images for the comparison study.

3D Dynamic Keyhole Imaging with a Library of the Prior Data

FIG. 10 shows the scheme of the 3D dynamic keyhole imaging. The dynamic keyhole imaging uses a library of prior peripheral k-space data in combination with keyhole k-space data acquired in real-time. For high-spatial, high-temporal 3D dynamic keyhole imaging, high spatial and temporal resolution prior k-space data at various respiratory positions were needed as a library of the prior data in 3D dynamic keyhole imaging.

Twenty real-time volumetric 3D MRI datasets from each of four human subject were used in the comparison study. Each dataset included low-spatial, high-temporal resolution images from the acquisition and high-spatial, high-temporal resolution images generated using the SRG model. Respiratory displacement was extracted from the profile of the diaphragm on the coronal middle slice of the high-spatial, high-temporal resolution 3D MRI. Based on each subject's respiratory patterns, approximately 10 respiratory positions were sampled through a couple of respiratory cycles. The corresponding high-spatial high-temporal resolution MRI datasets were used as the prior data associated with the respiratory position. The remaining high-spatial, high-temporal resolution MRI datasets were used as the temporal data in the 3D dynamic keyhole imaging.

In the simulation studies, all SR image data were Fourier transformed into k-space. Approximately 10 volumetric SR MR k-space datasets were used as the prior k-space dataset and the remaining volumetric SR MR k-space datasets were used as the temporal k-space datasets. The size of the keyhole k-space data was empirically determined in consideration of image quality and time. The k-space data matrix (kx×ky×kz) was 256×256×10. The size of keyhole k-space data was 26 ky lines/slice. The size of the prior peripheral k-space data was 230 ky lines/slice. The prior peripheral and keyhole k-space data were matched based on respiratory displacements to accelerate acquisition time and improve image quality in the presence of motion. Images were reconstructed using the conventional 3D Fourier-transform with the combined full k-space dataset.

Comparison Studies and Evaluation

The efficacy of the 3D dynamic keyhole imaging with super-resolution (SR_dKeyhole) was compared with zero-filling reconstruction (zero-filled in the k-space data periphery), conventional keyhole reconstruction with low-spatial, high-temporal prior data (LR_cKeyhole), and conventional keyhole reconstruction with super-resolution prior data (SR_cKeyhole) using MATLAB R2018b (The MathWorks, Natick, USA). All reconstruction techniques used high-spatial resolution central k-space data.

The quality of the reconstructed images with each of four methods was compared with the ground-truth SR images using the original full k-space data. Image quality and artifacts were evaluated using: (1) image intensity difference, (2) structural similarity index (MATLAB function: SSIM), and (3) average value of image relative error (IRE). SSIM assesses images in terms of luminance, contrast, and structural comparisons; a SSIM value of 1 indicates the reconstructed image and the original image are identical.

$$IRE = \sqrt{\Sigma_{x,y,z}[I_{original}(x,y,z) - I_{recon}(x,y,z)]^2} / \sqrt{\Sigma_{x,y,z}[I_{original}(x,y,z)]^2} \quad (1)$$

where $I_{original}$ is the original image and $I_{recon}$ is the reconstructed image in equation (1). An IRE value of 0 indicates the reconstructed image and the original image are identical.

Figure 8:
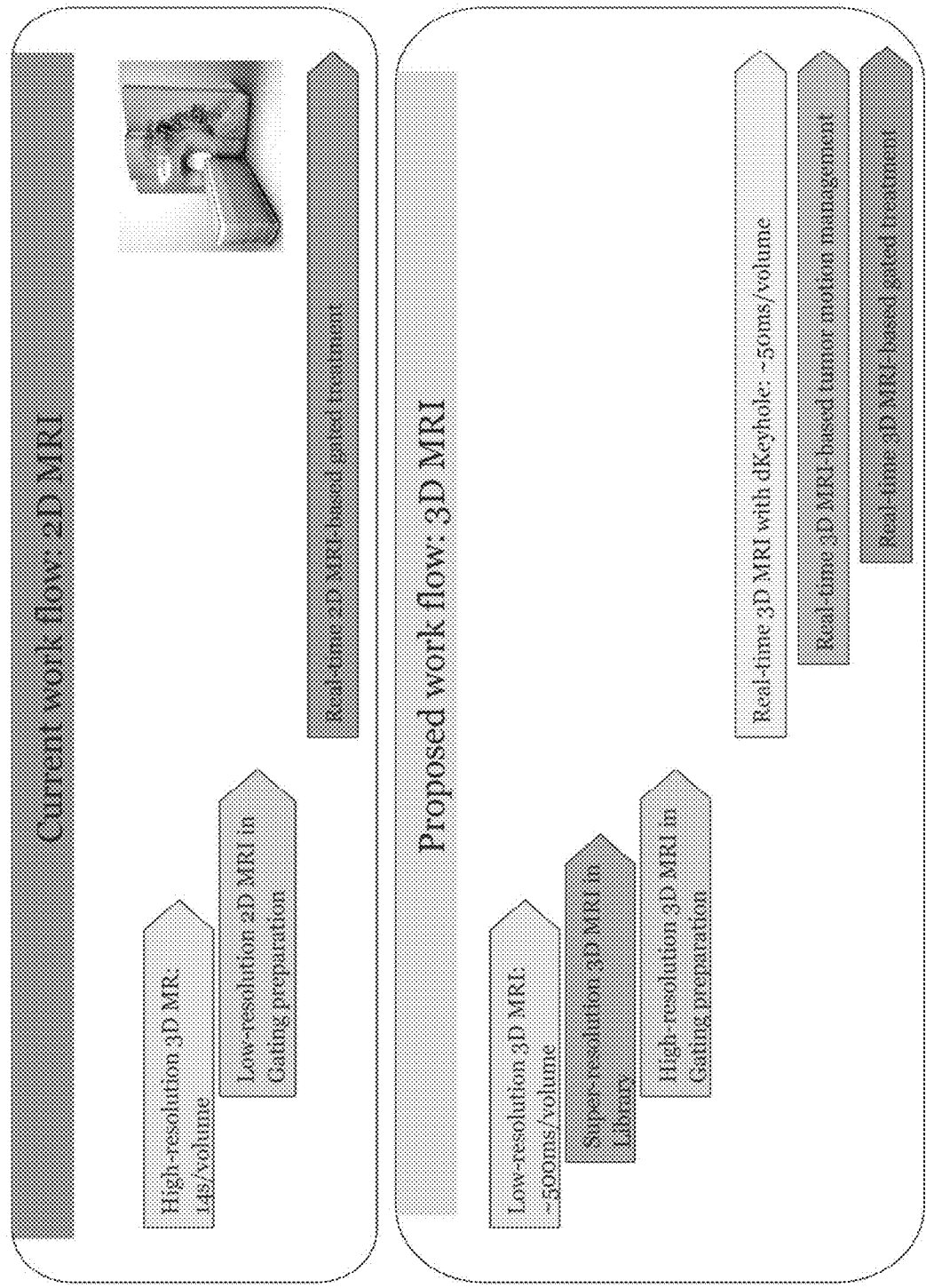
FIG. 8 contains schematics of a current 2D MRI workflow and the disclosed 3D MRI workflow.

Example 2: Real-Time 3D MRI Using Dynamic Keyhole and Super-Resolution Techniques This example describes the differences between current 2D MRI techniques and the unique real-time 3D MRI technique described above. FIG. 8 shows the advantages in using the real-time 3D MRI technique compared to current techniques.

What is claimed is:

1. A computer-aided method of generating a real-time 3D magnetic resonance (MR) image of a subject comprising:
   obtaining a keyhole 3D MR image of the subject, the keyhole 3D MR image comprising a k-space central dataset;
   transforming, using a computing device, the keyhole 3D MR image into a super-resolution 3D MR image using a deep-learning super-resolution generative (SRG) model;
   extracting, using the computing device, a respiratory phase of the super-resolution 3D MR image;
   combining, using the computing device, an SR k-space central dataset corresponding to the super-resolution 3D MR image with a respiratory phase-matched k-space peripheral dataset retrieved from a stored library of k-space peripheral datasets to produce a combined k-space dataset; and
   reconstructing, using the computing device, the real-time 3D MR image from the combined k-space dataset.

2. The method of claim 1, wherein the k-space central dataset comprises reduced k-space data relative to a high-resolution 3D MR image, the reduced k-space data comprising reduced kx data, reduced ky data, reduced kz data, and any combination thereof.

3. The method of claim 2, wherein each peripheral k-space dataset of the library comprises a k-space dataset corresponding to a high-resolution 3D MR image with the k-space central dataset removed.

4. The method of claim 3, further comprising obtaining the stored library of k-space peripheral datasets by:
   obtaining a plurality of high-resolution 3D MR images of the subject;
   extracting, using the computing device, an index respiratory phase from each high-resolution 3D MR image;
   removing, using the computing device, each k-space central dataset from each k-state dataset of each of high-resolution 3D MR images to produce each k-space peripheral dataset;
   assembling, using the computing device, each k-space peripheral dataset and each corresponding index respiratory phase from each high-resolution 3D MR image to produce the stored library of k-space peripheral datasets.

5. The method of claim 1, wherein the deep-learning super-resolution generative (SRG) model comprises a generator portion of a cascading deep learning model trained using a generative adversarial network framework with a training dataset of matched low resolution and high resolution MR images.

6. The method of claim 1, further comprising denoising, using the computing device, the keyhole 3D MR image using a denoising autoencoder (DAE), the DAE comprising a convolutional neural network (CNN).

7. The method of claim 1, wherein extracting the respiratory phase further comprises extracting, using the computing device, a profile of the diaphragm on a middle coronal slice of the super-resolution 3D MR image.

8. The method of claim 1, wherein extracting the respiratory phase further comprises extracting, using the computing device, a 1D Fourier transform of a kx line at a ky-kz center of the k-space central dataset.

9. The method of claim 1, wherein the real-time 3D MR image is reconstructed using a 3D Fourier-transform of the combined k-space dataset.

10. The method of claim 1, wherein the real-time 3D MR image of the subject includes a target region of the subject, the target region comprising a tumor, and organ, a tissue, any portion thereof, and any combination thereof.

11. The method of claim 1, wherein the image is generated in the presence of motion.

12. A computer-implemented method of treating a subject in need thereof comprising:
   generating real-time 3D MR images of the subject by:
      obtaining a keyhole 3D MR image of the subject, the keyhole 3D MR image comprising a k-space central dataset;
      transforming, using a computing device, the keyhole 3D MR image into a super-resolution 3D MR image using a deep-learning super-resolution generative (SRG) model;
      extracting, using the computing device, a respiratory phase of the super-resolution 3D MR image;
      combining, using the computing device, an SR k-space central dataset corresponding to the super-resolution 3D MR image with a respiratory phase-matched k-space peripheral dataset retrieved from a stored library of k-space peripheral datasets to produce a combined k-space dataset; and
      reconstructing, using the computing device, the real-time 3D MR image from the combined k-space dataset; and
   at least one of: managing motion of a subject or a tumor in the subject using the generated real-time 3D MR images, gating a treatment of a subject or a tumor in the subject using the real-time 3D MR images, and any combination thereof.

13. The method of claim 12, wherein the k-space central dataset comprises reduced k-space data relative to a high-resolution 3D MR image, the reduced k-space data comprising reduced kx data, reduced ky data, reduced kz data, and any combination thereof.

14. The method of claim 13, wherein each peripheral k-space dataset of the library comprises a k-space dataset corresponding to a high-resolution 3D MR image with the k-space central dataset removed.

15. The method of claim 14, further comprising obtaining the stored library of k-space peripheral datasets by:

obtaining a plurality of high-resolution 3D MR images of the subject;

extracting, using the computing device, an index respiratory phase from each high-resolution 3D MR image;

removing, using the computing device, each k-space central dataset from each k-state dataset of each of high-resolution 3D MR images to produce each k-space peripheral dataset;

assembling, using the computing device, each k-space peripheral dataset and each corresponding index respiratory phase from each high-resolution 3D MR image to produce the stored library of k-space peripheral datasets.

16. A system for generating a real-time 3D MR image of a subject, the system comprising:

a computing device comprising at least one processor, the at least one processor configured to:

obtain a keyhole 3D MR image of the subject, the keyhole 3D MR image comprising a k-space central dataset;

transform, using a computing device, the keyhole 3D MR image into a super-resolution 3D MR image using a deep-learning super-resolution generative (SRG) model;

extract, using the computing device, a respiratory phase of the super-resolution 3D MR image;

combine, using the computing device, an SR k-space central dataset corresponding to the super-resolution 3D MR image with a respiratory phase-matched k-space peripheral dataset retrieved from a stored library of k-space peripheral datasets to produce a combined k-space dataset; and reconstruct, using the computing device, the real-time 3D MR image from the combined k-space dataset.

17. The system of claim 16, wherein the k-space central dataset comprises reduced k-space data relative to a high-resolution 3D MR image, the reduced k-space data comprising reduced kx data, reduced ky data, reduced kz data, and any combination thereof.

18. The system of system 17, wherein each peripheral k-space dataset of the library comprises a k-space dataset corresponding to a high-resolution 3D MR image with the k-space central dataset removed.

19. The system of claim 18, further comprising a magnetic resonance imaging (MRI) scanner obtaining the keyhole 3D MR image of the subject.

\* \* \* \* \*